United States Patent [19]

Majima et al.

[11] 4,102,911

[45] Jul. 25, 1978

[54] SULFONATING OR SULFATING METHOD

[75] Inventors: Kanji Majima; Kensuke Takei; Keiichi Tsutoo, all of Wakayama, Japan

[73] Assignee: Kao Soap Co., Ltd., Tokyo, Japan

[21] Appl. No.: 243,874

[22] Filed: Apr. 13, 1972

Related U.S. Application Data

[63] Continuation-in-part of Ser. No. 739,010, Jun. 21, 1968, abandoned.

[30] Foreign Application Priority Data

Jun. 26, 1967 [JP] Japan .................................. 42-40928

[51] Int. Cl.² .......................................... C07C 139/04
[52] U.S. Cl. ................................. 260/458 R; 260/400; 260/401; 260/456 R; 260/456 P; 260/457; 260/459 R; 260/460; 260/505 A; 260/505 E; 260/505 S; 260/512 R; 260/513 T
[58] Field of Search .......... 260/457, 458, 459, 513 R, 260/505 S, 460, 505 A, 512 R, 513 N, 513 T, 400, 401, 456 R, 456 P, 505 E, 512 T; 23/285

[56] References Cited

U.S. PATENT DOCUMENTS

| 2,828,331 | 3/1958 | Marisic et al. ............... 260/505 S X |
| 2,923,728 | 2/1960 | Falk et al. ............................ 260/459 |
| 3,270,038 | 8/1966 | Marshall et al. ................. 260/459 X |
| 3,396,204 | 8/1968 | McCarty et al. .................. 23/285 X |

FOREIGN PATENT DOCUMENTS 1,576,626   8/1969   France ................................ 260/459

*Primary Examiner*—Norman Morgenstern
*Attorney, Agent, or Firm*—Blanchard, Flynn, Thiel, Boutell & Tanis

[57] ABSTRACT

A method for reacting sulfur trioxide and sulfateable or sulfonateable liquid organic compounds such as alcohols, and unsaturated or aromatic compounds is disclosed which comprises contacting said organic liquid with a gaseous mixture of from 2 to 20% by volume of sulfur trioxide and the balance an inert gas diluent, in a vertical cylindrical reaction zone that is at least about 25 mm. in diameter and comprises a straight cylinder having a gas-liquid contact length of at least 1.5 meters and having an annular inlet means for the liquid at the lower end of the reaction zone; the contact being effected by means of an upward stream of the gaseous mixture having sufficient velocity to form the liquid into a rising annular film throughout the length of the zone.

6 Claims, 2 Drawing Figures

SULFONATING OR SULFATING METHOD

CROSS REFERENCE TO RELATED APPLICATIONS

This application is a continuation-in-part of our copending application Ser. No. 739,010, filed June 21, 1968, now abandoned.

BACKGROUND OF THE INVENTION

1. Field of the Invention

This invention relates to a method of sulfating or sulfonating liquid organic materials.

2. Description of the Prior Art

The sulfonation or sulfation of organic compounds has been carried out in gas-liquid contact processes that use horizontally disposed reaction zones inside which the liquid is made to flow in a turbulent annular path, driven by a gaseous mixture of sulfur dioxide and an inert gas. Also, gas-liquid hydrobromination reactions have been carried out in a process which calls for contact between gaseous hydrogen bromide and a thin turbulent film of the liquid reactant. The film, in this prior process, can be a rising annular film, a concurrent or countercurrent falling film, a horizontally propelled film or the like.

Of these prior gas-liquid reactions that involve concurrent annular flow of the vertical or horizontal type all have been heretofore carried out in cylindrical reaction vessels or relatively small cross section. This is particularly true of the above-mentioned sulfation which is carried out in horizontal tubes of about 5 mm. diameter Use of small diameter reaction zones has limited the capacity of the reaction vessel, has increased its cost, and has complicated its maintenance. Moreover, while representing improvements over other gas-liquid reaction methods, these small diameter reaction zones are limited in the completeness or reaction and quality of reacted product they can achieve as evidenced by charring or the formation of colored by-product impurities. These latter limitations in the case of the sulfonation or sulfation are believed by the applicants to be caused by the unevenness of the reaction in the smaller sized tubes, caused in turn by non-uniform flow. Applicants have found in this reaction that, generally speaking, the greater the velocity the better is the degree of completion of the reaction. In horizontally disposed reaction zones the bias of the flow owing to gravity must be overcome by the use of small diameter reaction zones coupled with turbulence to achieve annular (called "turbannular") flow. This factor of bias of gravity must be balanced by a maximum gas flow rate above which the flow of the liquid ceases to be uniform.

In a sulfonation or sulfation reaction the recovery of unreacted materials and their reuse are very difficult, and also the removal from the reaction product of colored by-product impurities (decoloration) is difficult and uneconomical. Therefore, it is required to increase the degree of completion of reaction and prevent the formation of colored by-product impurities as much as possible.

SUMMARY OF THE INVENTION

The present invention is based on the discovery that by reacting sulfur trioxide and a liquid organic compound capable of being sulfated or sulfonated, by contacting the organic liquid with a gaseous mixture of from 2 to 20% by volume of sulfur trioxide and the balance a gas that is inert in the reaction, in a vertical cylindrical reaction zone that is at least 25 mm. in diameter and comprises a straight cylinder having a gas-liquid contact length of at least 1.5 meters, unexpectedly improved results are achieved compared with a corresponding reactor positioned horizontally. In the process the gas current velocity in the reaction zone is 20 meters per second or more so that an annular film of the liquid reactant is formed and rises along the inside wall of the reactor.

The reaction zone has a diameter of at least about 25 mm. Although larger diameters can be used, normally the maximum diameter of the cylindrical reaction zone is about 100 mm; because it is more economical to use several reaction zones in parallel than to provide one reaction zone of extremely large diameter.

The gas-liquid contact length increases as the diameter of the reaction zone increases. The optimum ranges of gas-liquid contact length of the reaction zone are:

Diameter of reaction zone Length of gas-liquid contact zone
25 mm. — 1.5–4 m.
50 mm. — 3–15 m.
100 mm. — 8–35 m.

Thus, when a liquid raw material which can be sulfonated or sulfated and a sulfur trioxide-containing gas stream consisting of sulfur trioxide and air or other gas inert to the reaction, such as nitrogen or carbon dioxide, said stream containing from about 2 to about 20% by volume of sulfur trioxide, are continuously introduced from below into a fixed vertical cylindrical reaction zone, preferably a jacketedd tube, having the dimensions indicated above, and the velocity of the gas stream is about 20 to about 130 meters per second, preferably between 40 and 110 meters per second, the gas will effect a driving force to form a rising annular film of the organic reactant material to be sulfonated or sulfated in the reaction tube and the mixing and cooling of the reactants on the reactor wall surface in the reaction zone will take place ideally.

Owing to the fact that the rising annular film is raised evenly against gravity because of the vertical disposition of the wall surface, the liquid of the film is continuously and evenly mixed within itself, and a complete reaction, with very little evidence of said reaction, is effected. Under the above reaction conditions, the thickness of the rising annular film is in the range of from about 0.012 to 0.10 cm.

In conducting a sulfonating or sulfating reaction by the method of the present invention, one or, as required, two or more reaction tubes, connected in parallel, are held in a substantially vertical position. The reaction tube is provided with a jacket so that heat exchange can be effectively carried out by using a proper coolant. Alternatively, the reaction tube can be made as a double cylinder consisting of an outer cylinder having a cooling jacket on the outside and an inner cylinder which can be used as an inner heat-exchanging jacket, in which case the annular space between the outer cylinder and inner cylinder serves as the reaction zone.

Since the sulfating or sulfonating reaction is generally a markedly exothermic reaction, it is necessary to construct the reaction tube to cool the reactants by using a cooling medium so that the temperature can be sufficiently controlled.

According to the present invention, when a liquid organic raw material to be sulfated or sulfonated and a gas current of a diluted sulfur trioxide gas are introduced into the lower part of the reaction tube in parallel flow from below, the reaction material is vigorously mixed with the gas by the driving force of the gas near the nozzle from which the gas current is blown in. There is formed a rising annular liquid film and a gas current in the region inside the film, the liquid film is spread over the inner wall of the reaction tube and rises while the film is agitated by the gas current to continuously explore new reaction surface areas or zones and to mix the liquid together with the driving gas current at the interface therebetween. The reaction is completed before or at the time the liquid film reaches the uppermost part of the reaction tube.

In the above process the gas-liquid contact begins at the point at which the $SO_3$-containing gas current is blown in through the nozzle. However, the liquid organic raw material to be reacted can be also blown in together with an inert gas, such as air, nitrogen and carbon dioxide, in the bottom of the reaction zone so that a rising annular film of the liquid reactant is formed in the reaction tube and then $SO_3$ gas or a diluted gas containing $SO_3$ in a high concentration can be introduced higher up in reaction zone so as to come into contact with the film.

The conditions for producing the rising annular film will vary depending on the physical properties of the reactants, that is, the organic compounds to be reactd and the $SO_3$—containing gas mixture, and the properties of the reaction products to be formed. But generally, when the gas current velocity is more than 20 m./sec., usable annular film is formed.

Further, if the gas current velocity is more than 40 m./sec., the annular rising film of the liquid organic reactant is formed more uniformly distinctly and, consequently, remarkably high reaction rates are obtained. In these cases it should be noted that the annular film is not only moved up along the inner wall of the tube, but the reacting liquid mixture rises while rotating or moving circumferentially over the wall in such a manner that the film surface that contacts the wall is continuously stripped off from the wall surface and the liquid film is continuously mixed within itself.

However, if the gas current velocity is more than 130 m./sec., a portion of the organic compound will be converted to a mist state. This mist may be mixed with or contained in the $SO_3$—containing gas mixture so that it will react with $SO_3$ excessively, thereby causing so-called charring of the product which might cause undesirable coloring of the reaction product. Also, the mist may be exhausted and lost in the gas discharged from the reaction system which is obviously undesirable economically.

In contrast to the procedure according to the invention, if the substances to be reacted are introduced from above and the inert gas is used as a driving gas, an annular film may be produced, but the phenomenon of stripping off the layer of film from the tube wall will occur to a minor extent, if at all, and the gas-liquid contact and mixing will not be sufficient. Further, it the reaction tube or the double cylinder type reaction tube is set horizontally, a film may be formed by the action of the driving gas but the film material will tend to fall down in the tube due to gravity and this will cause nonuniformity of the thickness of the film, which will be undesirable in respect of the gas-liquid mixing.

The mol ratios of $SO_3$ to 1 mol of the liquid organic material which is to be sulfonated or sulfated should be generally within the range of from 0.9 to 1.20, preferably, from 1.0 to 1.15. The reaction temperature will be selected within the range of 40° to 100° C., depending on the organic reactant used.

DESCRIPTION OF THE PREFERRED EMBODIMENTS

The process according to the present invention as described above will be more clearly understood by the following further explanation and by reference to the accompanying drawings.

In the drawings

Figure 1:
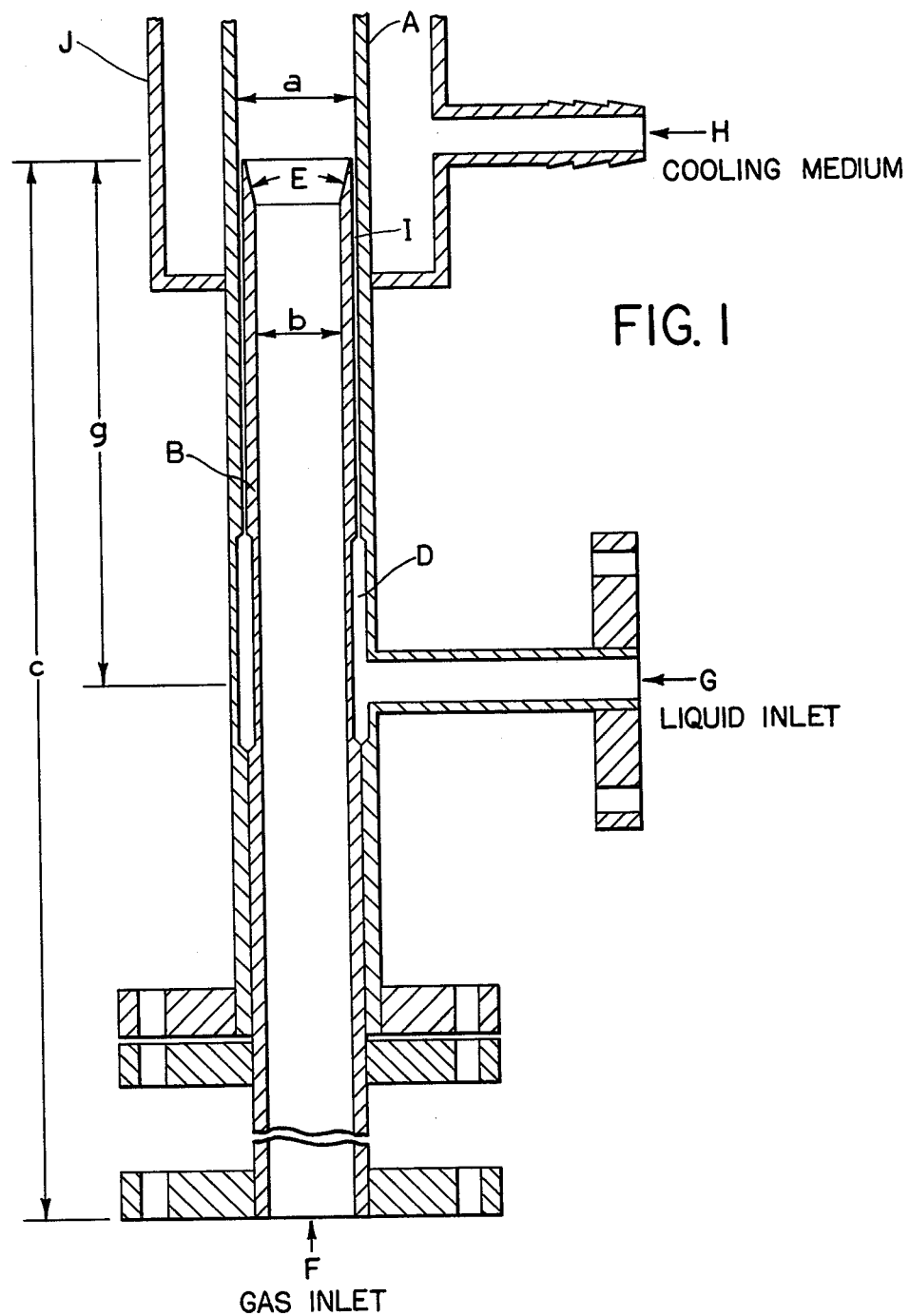
FIG. 1 is a schematic central sectional view showing an embodiment of the raw material introducing part of a vertical cylindrical reactor which is adapted to carry out the method of the present invention.

It will be apparent that FIG. 1 illustrates one example of a suitable raw material introducing and mixing portion. The structure of the apparatus is not limited to the specific structural features illustrated.

In FIG. 1, $a$ is the inside diameter of a reaction tube A, $b$ is the inside diameter of a gas feeding tube B and $c$ is the length of the gas feeding tube which functions as a gas current rectifying part. It is preferable that $c > 10 \times b$. D is a liquid chamber. E is an angle of expansion which may preferably be made about 10°. F is a gas inlet. G is a liquid inlet. H is a cooling medium inlet. J is a jacket and I is a clearance between the inner wall of the tube A and the outer wall of the gas feeding tube B.

As stated above, the dimension $a$ is at least about 25 mm. and normally is less than about 100 mm. The relation between the dimensions $a$ and $b$ is $$1 < a/b < 1.5$$

$g$ is the vertical distance from the liquid inlet G to the upper end of the gas feeding tube B. It is preferable that the dimension $g$ is $$b < g < 3 \times b$$

It is preferable to make $b$ as large as possible within the limits of possibility of manufacture. However, $b$ is usually less than 100 mm. for economic reasons. It is sometimes easier to control the process by providing a plurality of cylindrical reaction zones having diameters of 50 mm., connected in parallel for example, than to provide one reaction zone having an extremely large diameter of 150 mm., for example.

The effective length of the reaction zone or tube, as referred to herein, is the length of the straight gas-liquid contact zone. It is defined at the bottom by the inlet of the $SO_3$ containing reactant and at the top by the discharge of the reacted mixture. It can be discerned from FIG. 2, and can vary from about 1.5 to 4 meters or more for a reaction zone diameter of 25 mm., up to 35 meters for a zone of 100 mm. diameter.

Figure 2:
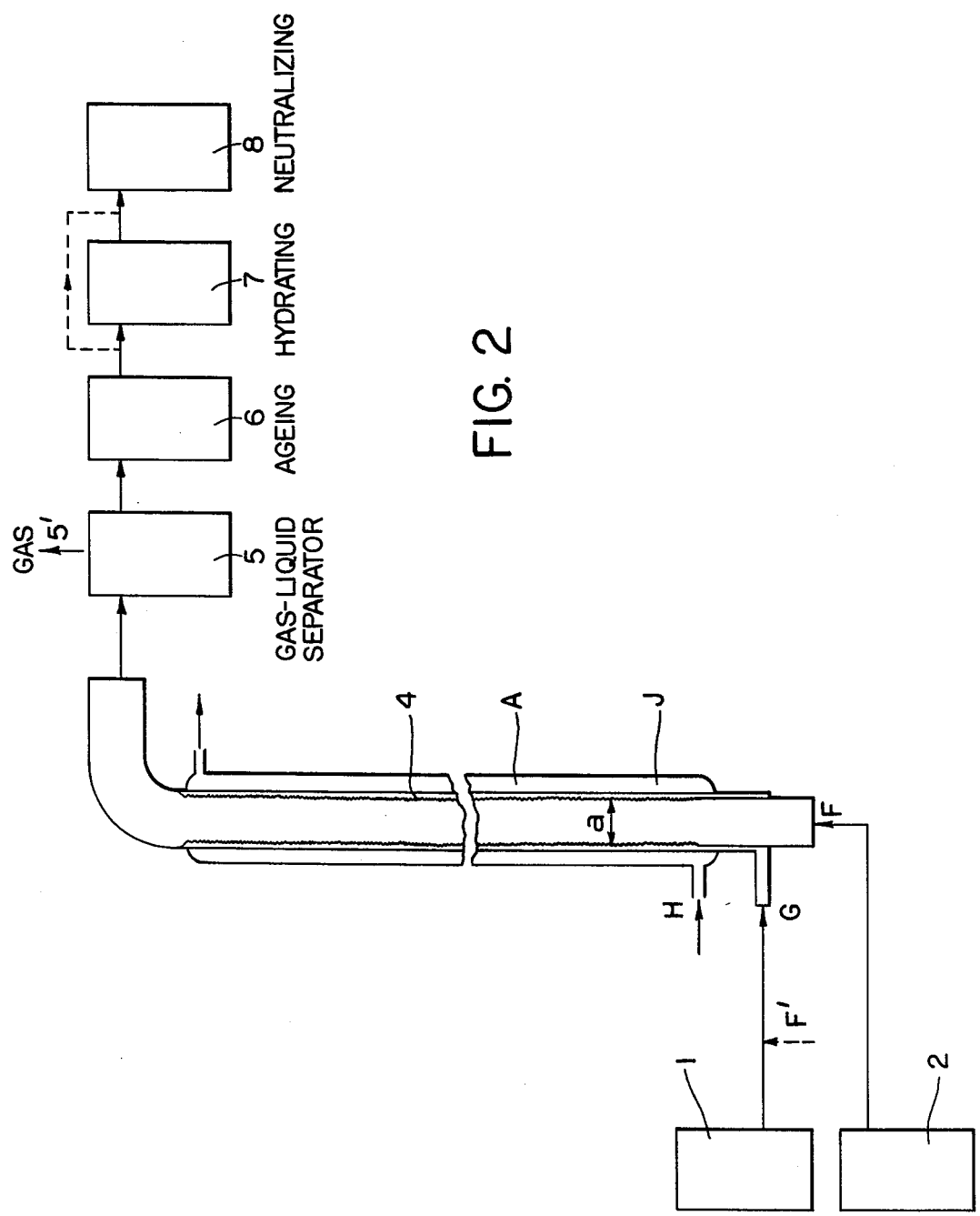
FIG. 2 is a block diagram showing schematically a typical process of the present invention.

In FIG. 2, A, F, G and J represent the same parts as are mentioned above. F′ is an inlet for introducing an inert gas into the organic raw reaction material. When an organic raw reaction material prepared in 1 and a gas mixture of $SO_3$ and an inert gas prepared in 2 are introduced into the reaction tube A through the raw material introducing mixing part, such as shown in FIG. 1, the liquid raw material will form a rising annular film 4 due to the driving force of the diluted $SO_3$ gas and a sulfating or sulfonating reaction will take place. The reaction product overflowing from the top part of the reaction zone, i.e., the vertical section of tube A will enter a gas-liquid separating and cooling part 5, will have the gas separated at 5', will be cooled, will pass through an aging part 6 (and, if necessary, through a hydrating part 7), and a neutralizing part 8 and will become a product.

The compounds which can be sulfated or sulfonated by the method of the present invention and which are liquid at normal (room) temperature or at the reaction temperature are:
1. A straight chain or branched chain alcohol having 8 to 20 carbon atoms or mixtures thereof,
2. A straight or branched alkyl benzene whose alkyl chain has from 8 to 25 carbon atoms or mixtures thereof,
3. A straight or branched chain olefin of 6 to 25 carbon atoms or mixtures thereof,
4. An alkylene oxide additive of an active hydrogen compound of an alcohol, phenol or fatty acid having 8 to 20 carbon atoms and 1 to 30 mols of alkylene oxide,
5. A fatty acid alkylolamide of 10 to 20 carbon atoms,
6. A fatty acid of 8 to 20 carbon atoms or mixture thereof or esters thereof with a lower alcohol or mixtures thereof,
7. A polyhydric alcohol ester of a fatty acid of 8 to 20 carbon atoms or its alkylene oxide derivatives.

For the gas containing $SO_3$ there can be used a stabilized sulfuric anhydride (such as, for example, that sold under the trademark "Sulfan" manufactured and sold by Allied Chemical Corporation) as evaporated and diluted with air or any other inert gas, such as nitrogen and carbon dioxide; or a so-called converter gas which is produced by converting a sulfur combustion gas as it is or as diluted. The proper concentration of $SO_3$ in the gas containing $SO_3$ is 2 to 20% by volume, preferably 2 to 10% by volume, the remainder being an inert gas diluent, such as air, nitrogen and carbon dioxide.

EXAMPLES 1 – 8

Tests were carried out using reaction tubes made of SUS 32 having the respective inside diameters as shown in the following table. Each vertical tube was vertically fixed and held, and it was connected to the top part with a gas-liquid separator through a tube for collecting the overflow of the reaction product. The length measurement was that of the gas-liquid contact length. The horizontal tubes had exactly the same dimensions and were horizontally fixed and were connected at the outlet with a tube for collecting the reaction product.

The organic raw material and reaction gas ($SO_3$ — air mixture) were introduced through their respective proportioning pumps from below into the reaction tube. The various organic compounds listed in the following table were thus made to react. The test conditions are shown in the following Table I.

Table I

| Organic reactant | Average molecular weight | Example No. | Reaction tube Inner diameter (mm) | Reaction tube Length (m) | Feed of organic reactant (Kg/Hr) | Diluted $SO_3$ gas Feed ($NM^3$/Hr) | Diluted $SO_3$ gas Volume ratio of $SO_3$/Air | Feeding temperature Organic reactant (° C) | Feeding temperature gas (° C) | Mol ratio of $SO_3$/organic reactant |
|---|---|---|---|---|---|---|---|---|---|---|
| Lauryl alcohol | 200 | 1 | 25 | 2 | 25.0 | 95.0 | 3/97 | 35 | 30 | 1.01 |
| Lauroxypoly-ethoxy-ethanol | 320 | 2 | 50 | 4 | 100 | 373 | 3/97 | 35 | 30 | 1.01 |
| | | 3 | 25 | 2 | 40.0 | 93.4 | 3/97 | 20 | 30 | 0.99 |
| | | 4 | 50 | 4 | 120 | 280 | 3/97 | 20 | 30 | 0.99 |
| | | 5 | 25 | 2 | 28.0 | 93.4 | 3/97 | 20 | 30 | 1.15 |
| Hexadecene | 224 | 6 | 50 | 4 | 100 | 333 | 3/97 | 20 | 30 | 1.15 |
| Straight chain alkyl benzene | 244 | 7 | 25 | 2 | 30.2 | 99.0 | 3/97 | 20 | 30 | 1.07 |
| | | 8 | 50 | 4 | 323 | 1060 | 3/97 | 20 | 30 | 1.07 |

The reactions were each carried out in duplicate for comparison, one using a vertical (V) reactor and one using a horizontal (H) reactor. All conditions such as cooling conditions of the duplicate reactions were controlled so as not to cause any difference in imposed reaction conditions between the apparatus disposed in a vertical position and the one arranged in a horizontal position. Cooling of the reaction zone was carried out by using a large volume of tap water (about 18° C). The results are given in Table II.

In the table, the reaction temperature at Inlet is the temperature at the beginning stage of the reaction and that at Outlet is at the end stage of the reaction.

The reaction temperatures, Inlet and Outlet, are the temperatures of the liquid film close to the inlet and close to the outlet. These were measured by inserting thermocouples contacting the liquid film on the opposite wall surface. Because the liquid film is very thin, the temperature measurements are approximations, but they indicate the pattern of temperature changes that occur. Generally speaking, because the reaction is exothermic, a lower Inlet temperature indicates that the reaction is not beginning as rapidly, while a higher Outlet temperature indicates that the reaction is still proceeding near the outlet. The more uniform temperature pattern achieved by the vertical apparatus indicates a more uniform reaction, leading to a more complete reaction and better product quality.

Table II

| Example No. | *1 Type of reactor | Reaction temperature Inlet (° C) | Reaction temperature Outlet (° C) | Gas velocity in tube (m/sec) | Moving velocity of film (m/sec) | Degree of completeness of reaction of Organic reactant (%) | Color of neutralized substance in Klett No. | Odor of neutralized substance |
|---|---|---|---|---|---|---|---|---|
| 1 | V | 41 | 49 | 43 | 0.5 | 96.8 | 24 | Moderate |
|   | H | 39 | 52 | 43 | 0.5 | 95.0 | 30 | " |
| 2 | V | 42 | 50 | 44 | 0.3 | 94.5 | 30 | " |
|   | H | 40 | 55 | 44 | 0.3 | 89.0 | 80 | " |

Table II-continued

| Example No. | *1 Type of reactor | Reaction temperature Inlet (°C) | Reaction temperature Outlet (°C) | Gas velocity in tube (m/sec) | Moving velocity of film (m/sec) | Degree of completeness of reaction of Organic reactant (%) | Color of neutralized substance in Klett No. | Odor of neutralized substance |
|---|---|---|---|---|---|---|---|---|
| 3 | V | 39 | 52 | 42 | 0.5 | 94.5 | 50 | " |
|   | H | 39 | 54 | 42 | 0.5 | 93.0 | 55 | " |
| 4 | V | 40 | 50 | 35 | 0.3 | 94.0 | 80 | " |
|   | H | 40 | 50 | 35 | 0.3 | 87.5 | 90 | " |
| 5 | V | 74 | 66 | 42 | 0.5 | 97.5 | 270 | " |
|   | H | 70 | 68 | 42 | 0.5 | 96.0 | 300 | " |
| 6 | V | 70 | 67 | 40 | 0.3 | 97.0 | 300 | " |
|   | H | 70 | 70 | 40 | 0.3 | 90.5 | 450 | " |
| 7 | V | 88 | 84 | 45 | 0.6 | 97.8 | 72 | No odor |
|   | H | 80 | 88 | 45 | 0.6 | 95.2 | 120 | " |
| 8 | V | 50 | 90 | 107 | 2.0 | 98.5 | 47 | " |
|   | H | 45 | 95 | 107 | 2.0 | 93.5 | 85 | " |

Note: *1
V: Vertical
H: Horizontal

The embodiments of the invention in which an exclusive property or privilege is claimed are defined as follows:

1. In a continuous gas-liquid reaction process for sulfating or sulfonating liquid organic reactant capable of being sulfated or sulfonated by reaction with gaseous sulfur trioxide and being selected from the group consisting of (1) straight chain or branched chain alcohol having 8 to 20 carbon atoms or mixtures thereof, (2) alkyl benzene whose alkyl chain has from 8 to 25 carbon atoms or mixtures thereof, (3) straight or branched chain olefin having 6 to 25 carbon atoms or mixtures thereof, (4) addition product of an alcohol, phenol or fatty acid having 8 to 20 carbon atoms and 1 to 30 mols of alkylene oxide, (5) fatty acid alkylolamide having 10 to 20 carbon atoms, (6) fatty acid having 8 to 20 carbon atoms, esters thereof with a lower alcohol or mixtures thereof, and (7) polyhydric alcohol ester of a fatty acid having 8 to 20 carbon atoms or its alkylene oxide derivatives, wherein said organic reactant is reacted with gaseous sulfur trioxide to obtain a corresponding sulfated or sulfonated reaction product, the improvement which comprises continuously flowing (A) an outer annular stream consisting of said liquid organic reactant upwardly through and substantially filling an annular space of small radial thickness defined between an outer cylindrical member and an inner cylindrical member and thence vertically into the lower end of an elongated vertical cylindrical reaction zone , and continuously flowing upwardly through said inner cylindrical member (B) an inner gaseous stream consisting of a mixture of about 2 to 20% by volume of sulfur trioxide and the balance a gaseous inert diluent, said streams flowing in concurrent substantially parallel vertically upwardly directed flow into and through said elongated vertical cylindrical reaction zone, the entirety of said gaseous stream being disposed within said inner cylinder and isolated from said organic reactant stream prior to entry of said streams into said reaction zone;

said streams flowing upwardly through said reaction zone in gas-liquid contact, said stream of liquid reactant forming a continuous thin annular upwardly rising outer liquid film of substantially uniform thickness on the wall of said reaction zone and extending the entire length thereof, said gaseous stream flowing inside of said liquid film upwardly through the entire length of the reaction zone and having a flow velocity in the range of from about 20 m./sec. to about 130 m./sec., said gaseous stream uniformly contacting said annular liquid film over its entire inner surface in said reaction zone to effect upward movement and mixing of said liquid film whereby the organic reactant and the gaseous sulfur trioxide are mixed and contacted with each other to effect the reaction, and rapidly extracting heat from the resultant reaction mixture as it passes upwardly through the reaction zone;

separating the liquid phase from the gaseous phase after same have left the top of the reaction zone and recovering the reaction product from the liquid phase.

2. A process as claimed in claim 1, in which the thickness of said annular liquid film is between 0.012 and 0.10 cm.

3. A process as claimed in claim 1, in which the gaseous stream has a flow velocity in the range of from about 40 m./sec. to 110 m./sec.

4. A process as claimed in claim 1, in which the mol ratio of sulfur trioxide to liquid organic reactant fed into the reaction zone is in the range of 0.9–1.20:1.

5. A process as claimed in claim 1, in which the reaction temperature of the reaction zone is maintained in the range of 40° to 100° C.

6. A process as claimed in claim 1, in which said annular stream of liquid organic reactant flowing upwardly through said annular space is cooled by indirect heat exchange with an externally applied coolant prior to entry of said annular stream into said reaction zone and the cooling is continued through said reaction zone.

* * * * *